(12) United States Patent
Sivan

(10) Patent No.: US 12,350,191 B2
(45) Date of Patent: Jul. 8, 2025

(54) COLD TREATMENT APPARATUS

(71) Applicant: FREEZE N FIT INC., Glen Cove, NY (US)

(72) Inventor: Avi Sivan, Glen Cove, NY (US)

(73) Assignee: FREEZE N FIT INC., Glen Cove, NY (US)

( * ) Notice: Subject to any disclaimer, the term of this patent is extended or adjusted under 35 U.S.C. 154(b) by 0 days.

(21) Appl. No.: 18/118,049

(22) Filed: Mar. 6, 2023

(65) Prior Publication Data

US 2023/0329901 A1 Oct. 19, 2023

Related U.S. Application Data

(63) Continuation of application No. 16/289,611, filed on Feb. 28, 2019, now abandoned, which is a continuation-in-part of application No. 16/207,996, filed on Dec. 3, 2018, now abandoned.

(60) Provisional application No. 62/593,657, filed on Dec. 1, 2017.

(51) Int. Cl.
*A61F 7/00* (2006.01)
*A61F 7/02* (2006.01)

(52) U.S. Cl.
CPC ...... *A61F 7/007* (2013.01); *A61F 2007/0075* (2013.01); *A61F 2007/0078* (2013.01); *A61F 2007/0087* (2013.01); *A61F 2007/029* (2013.01)

(58) Field of Classification Search
CPC .............. A61F 7/007; A61F 2007/0071; A61F 2007/0075; A61F 2007/0078; A61F 2007/0087; A61F 2007/0088; A61F 2007/0093; A61F 2007/0228; A61F 2007/029; A61F 2007/0295

See application file for complete search history.

(56) References Cited

U.S. PATENT DOCUMENTS

| | | | | |
|---|---|---|---|---|
| 11,141,219 | B1 * | 10/2021 | Schwarz | A61F 13/64 |
| 2008/0281307 | A1 * | 11/2008 | Donahue | A61N 5/0613 606/13 |
| 2011/0040235 | A1 * | 2/2011 | Castel | A61M 37/0092 604/20 |
| 2013/0238043 | A1 * | 9/2013 | Beardall | A61F 7/007 607/3 |
| 2014/0128780 | A1 * | 5/2014 | Kennedy | A61F 7/00 601/18 |
| 2014/0303608 | A1 * | 10/2014 | Taghizadeh | A61B 18/14 606/20 |
| 2017/0348143 | A1 * | 12/2017 | Rosen | A61F 7/007 |
| 2019/0167469 | A1 * | 6/2019 | Sivan | A61F 7/007 |
| 2019/0254866 | A1 * | 8/2019 | Whiteley | A61F 7/007 |
| 2019/0388707 | A1 * | 12/2019 | Shenfarber | A61F 7/007 |

* cited by examiner

*Primary Examiner* — Kaitlyn E Smith
*Assistant Examiner* — Bradford C. Blaise
(74) *Attorney, Agent, or Firm* — Collard & Roe, P.C.

(57) ABSTRACT

There is a chiller for cooling a human body down to dissolve fat on a person's body. There is a device which includes a housing. The housing has at least one handle, and is configured to at least partially house a cold plate. The cold plate is also chilled by a chiller disposed inside of the housing. The chiller is at least partially disposed in the housing and is configured to have access to at least one vent. The at least one vent is positioned on the housing. In at least one embodiment, the at least one vent is positioned opposite the cold plate.

14 Claims, 18 Drawing Sheets

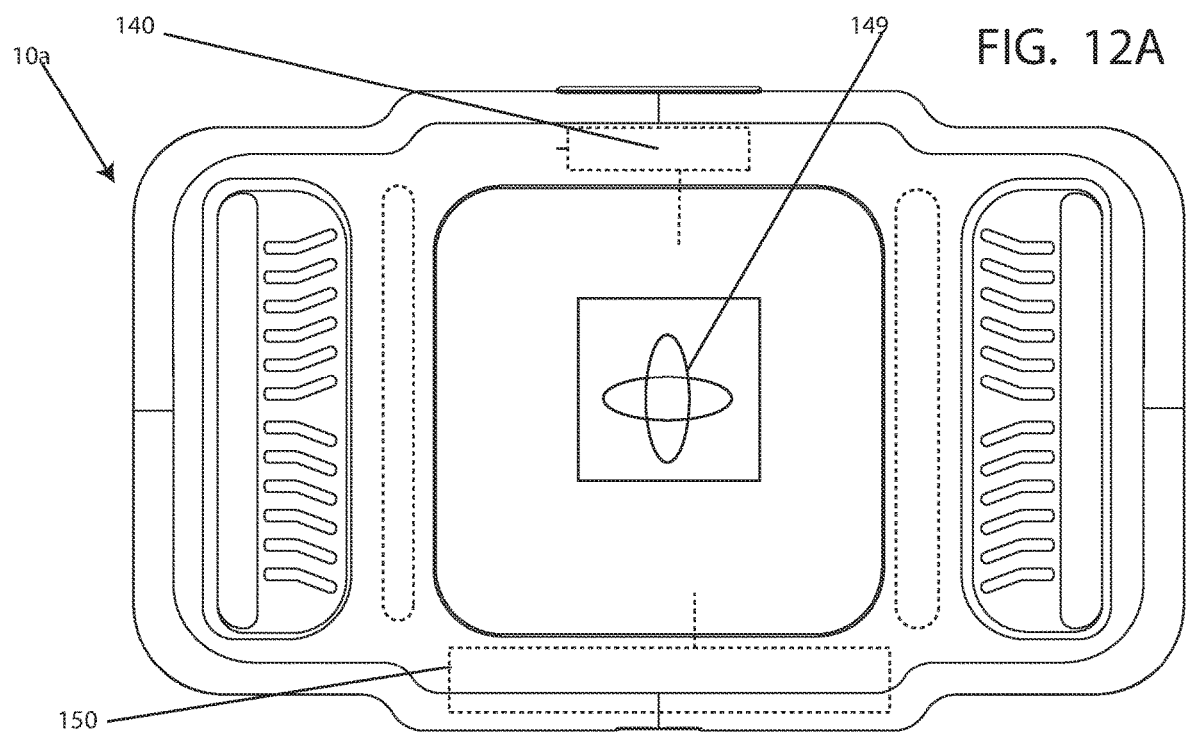
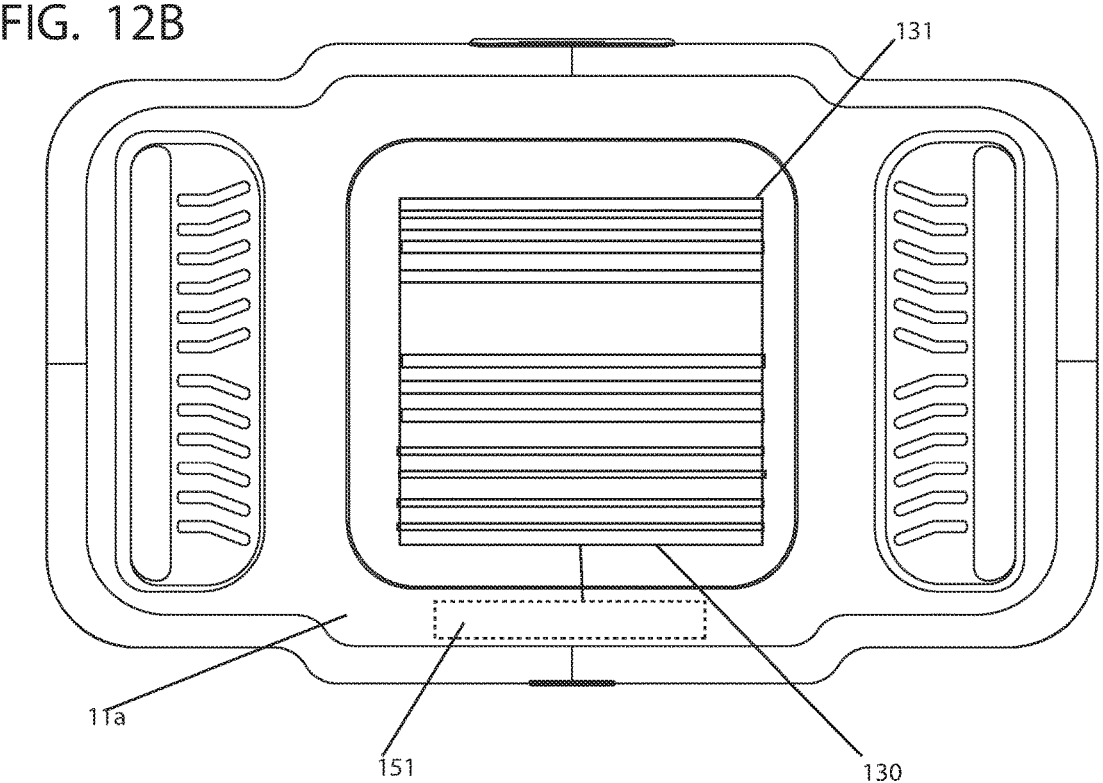

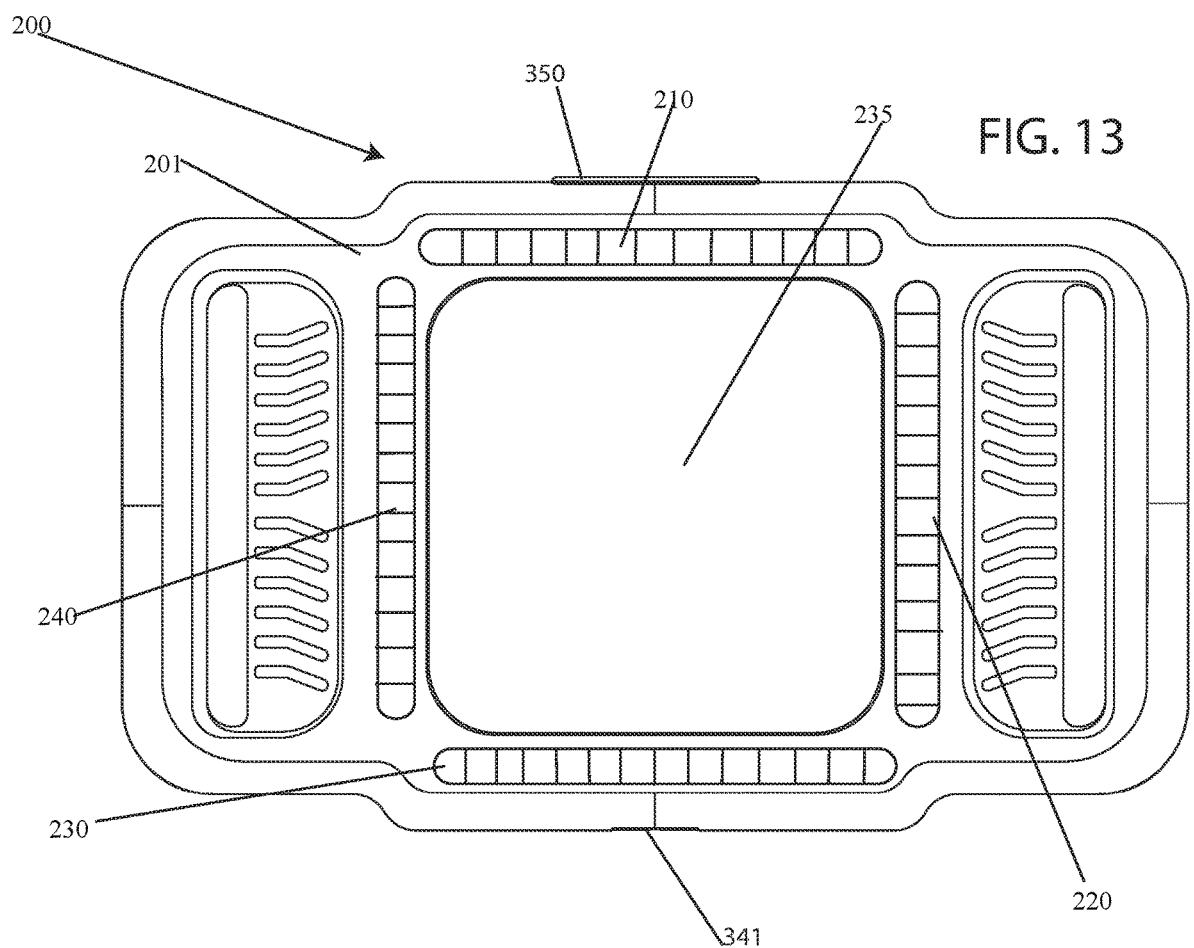

COLD TREATMENT APPARATUS

CROSS REFERENCE TO RELATED APPLICATIONS

This application is a continuation of U.S. patent application Ser. No. 16/289,611 filed on Feb. 28, 2019 (now abandoned), (hereinafter the '611 application); the '611 application is a continuation-in-part application of U.S. patent application Ser. No. 16/207,996 filed on Dec. 3, 2018 (now abandoned) (hereinafter the '996 application); the '996 application is a non-provisional application that claims priority from provisional application Ser. No. 62/593,657 filed on Dec. 1, 2017, the disclosures of the above applications are hereby incorporated herein by reference in their entirety.

BACKGROUND OF THE INVENTION

At least one embodiment of the invention relates to a chiller for cooling a human body down to dissolve fat on a person's body.

SUMMARY OF THE INVENTION

At least one embodiment of the invention relates to a chiller for cooling a human body down to dissolve fat on a person's body. There is a device which includes a housing. The housing has at least one handle, and is configured to at least partially house a cold plate. The cold plate is also chilled by a chiller disposed inside of the housing. The chiller is at least partially disposed in the housing and is configured to have access to at least one vent. The at least one vent is positioned on the housing. In at least one embodiment, the at least one vent is positioned opposite the cold plate.

The housing can have two handles and the vent can have at least two wings as well.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention. In the drawings, wherein similar reference characters denote similar elements throughout the several views:

FIG. 12A is a first open view of the device with the chiller plate and chiller removed showing a fan;

FIG. 12B is another open view of the device with the chiller being shown and the chiller plate being removed;

FIG. 13 is another view of another embodiment;

DETAILED DESCRIPTION OF PREFERRED EMBODIMENTS

Figure 1:
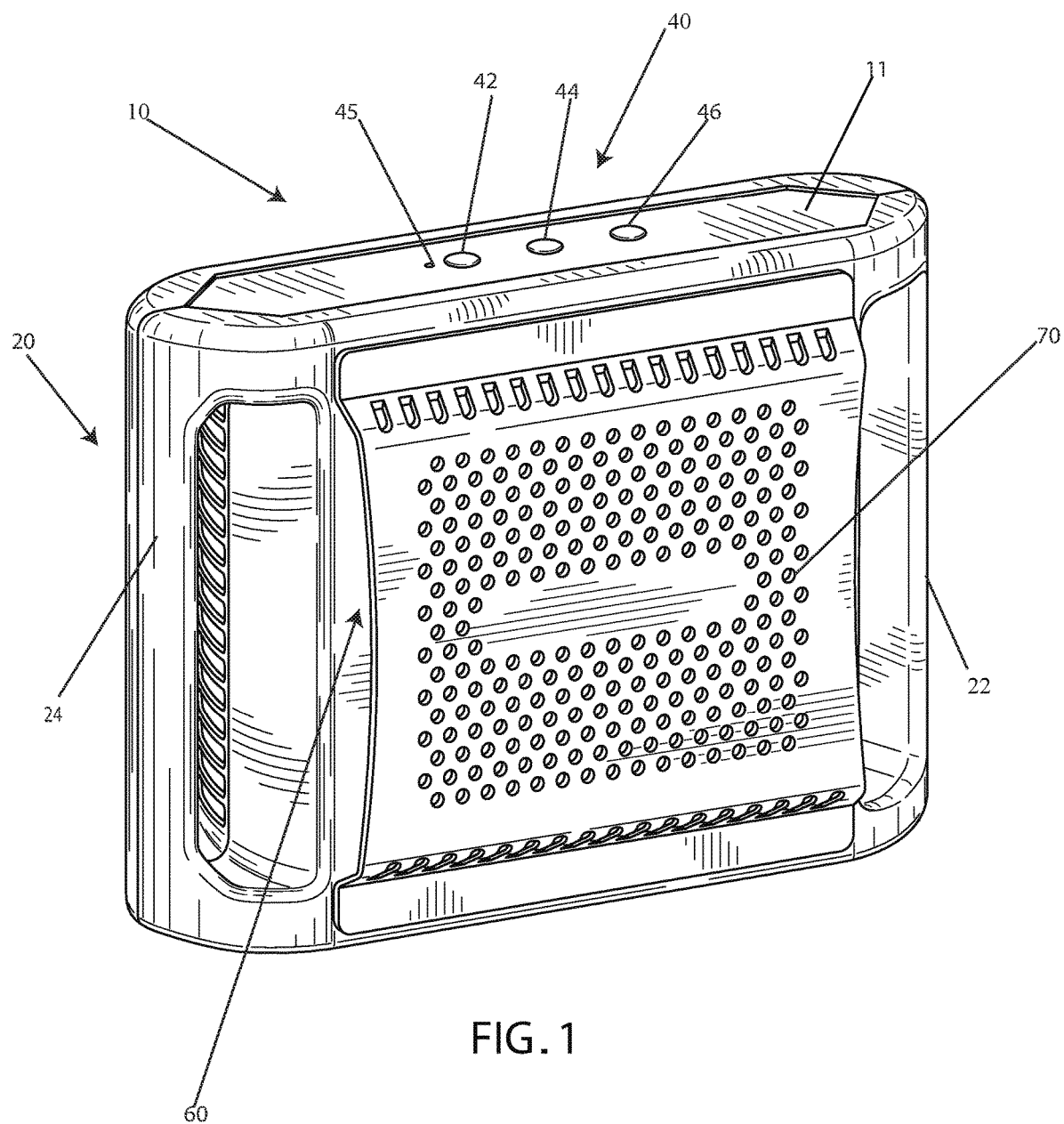
FIG. 1 is a front perspective view of the cold treatment device.

FIG. 1 is a front view of the cold treatment device. For example, in this 1 embodiment, there is shown a first embodiment 10 having a body or housing 11. Body or housing 11 can be made from any suitable material such as a plastic or polymer material. Other materials may be used such as a composite, rubber, or metal as well. The housing is configured to at least partially house at least one cold plate 30 (See FIG. 2). The housing is also configured to have at least two different handles 20 comprising a first handle 22 and a second handle 24. There are gaps 26 and 28 (See FIG. 5 which allow a user to place his hands around the handles 22 and 24. These handles can also be used to receive at least one strap as well. The strap 100 (See FIG. 10) is shown in greater detail in FIG. 3. There is also a controller 40 which has buttons to raise and lower the temperature and a plug connection or power port 50 (see FIG. 2) for receiving power from a power supply. For example, there is an on/off button 42, an up button 44, and a down button 46. On/off button 42 is also associated with light 45 to indicate whether the device is turned on or off.

Figure 2:
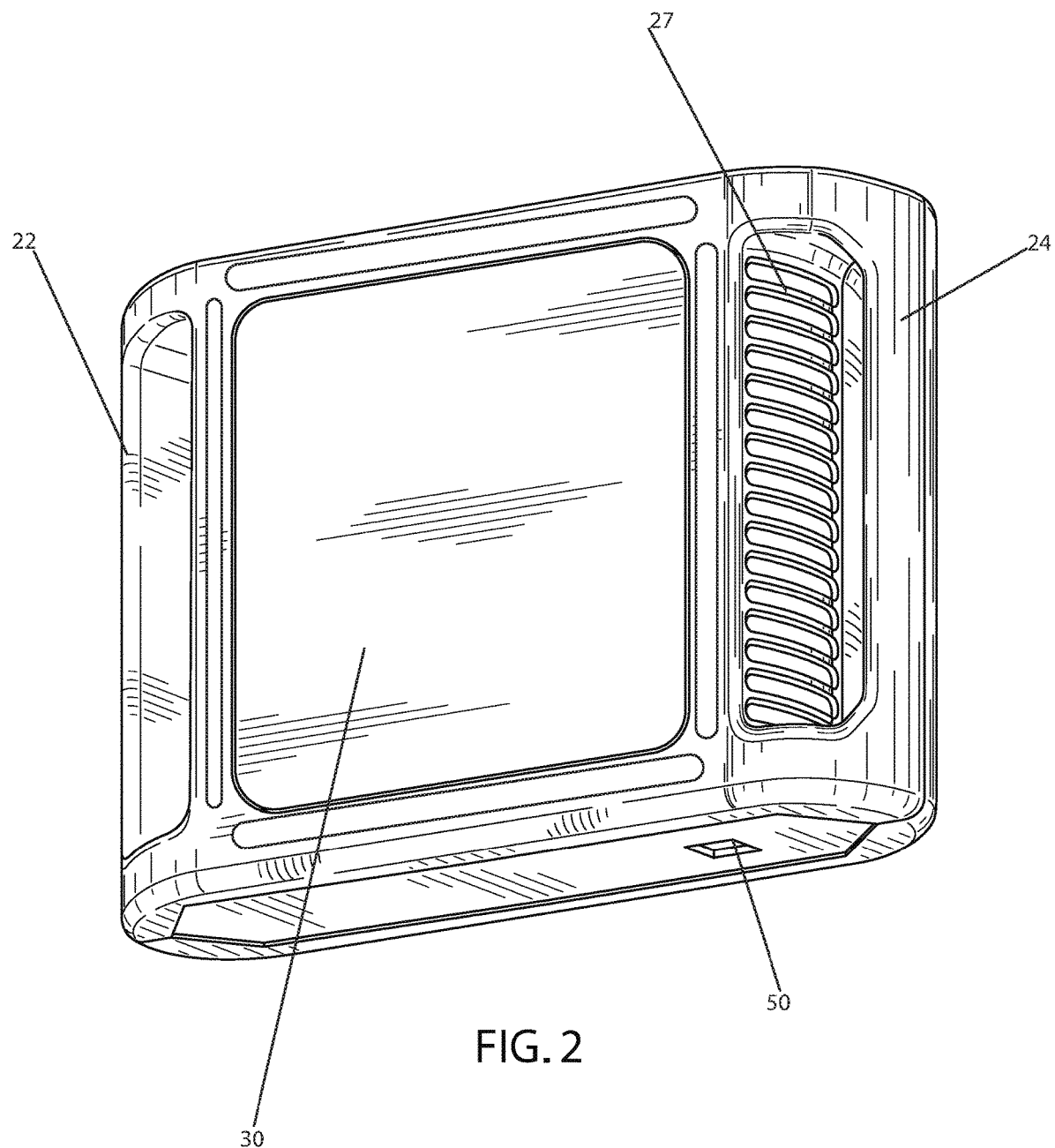
FIG. 2 is a back-perspective view of the cold treatment device.

FIG. 2 is a back view of the cold treatment device. In this view there is shown back side which has vents 27. These vents 27 and 29 (see FIG. 5) disposed near the gap regions 26 and 28. These vents are disposed on the first side adjacent to the cold plate 30. These vents are configured to displace heated air from the chiller 130 (See FIG. 11). The vents as described above are configured to vent air or other cooling fluid from the heat exchanger/chiller 130. In addition, in this view there is shown power supply port/plug connection 50 and buttons for controller 40.

Figure 3:
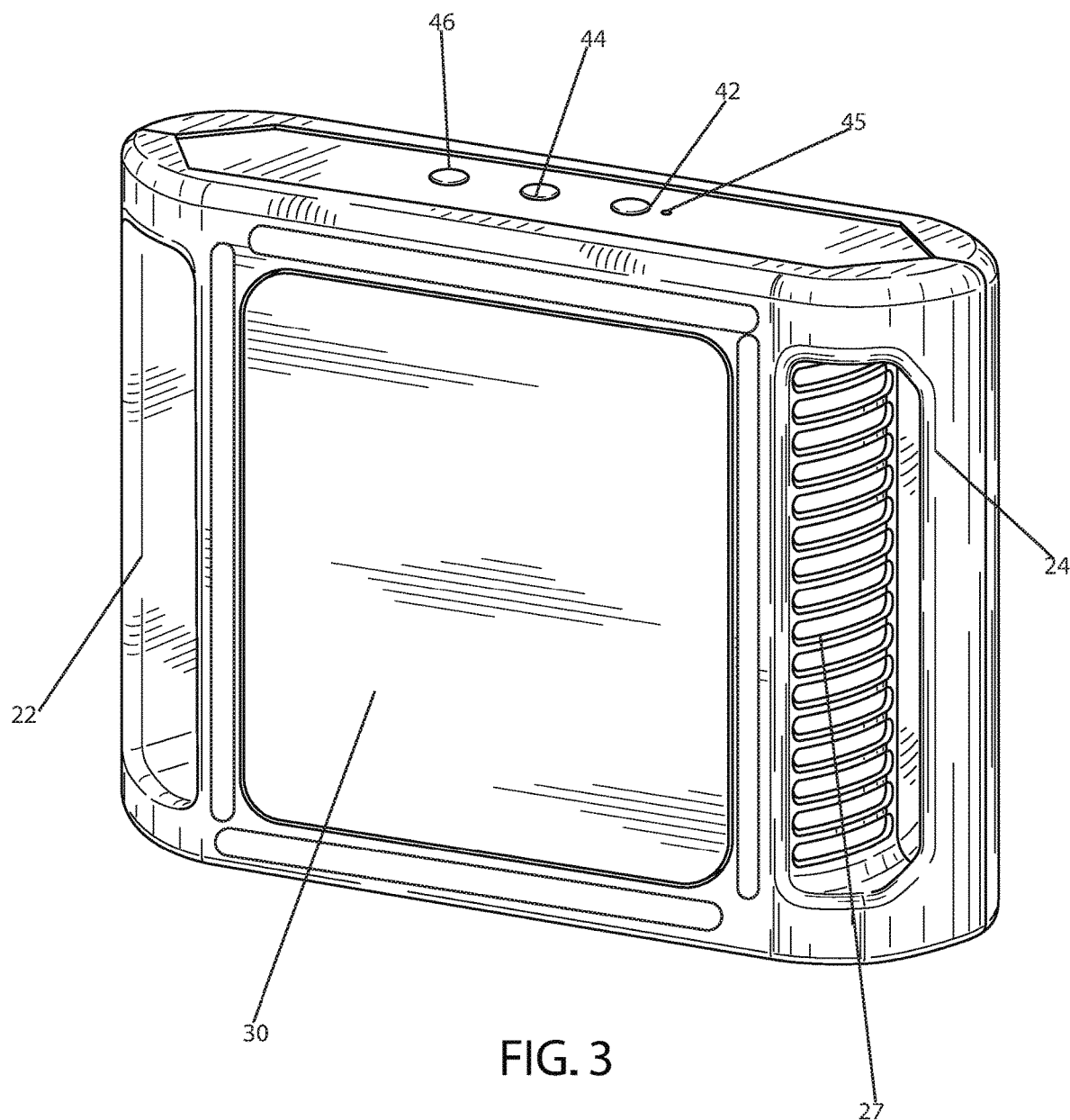
FIG. 3 is a back-top perspective view of the cold treatment device.

FIG. 3 shows a top view of the device which shows controller 40 having buttons 1 including an on/off button 42, an up button 44 and a down button 46. The up button 44 is configured to make the chill plate 30 cooler, while the down button is configured to make the chill plate warmer. In addition, on the back side of the device, there is shown vents 70 as well as wings 62 and 64 which are configured to be spaced from handles 22 and 24.

Figure 4:
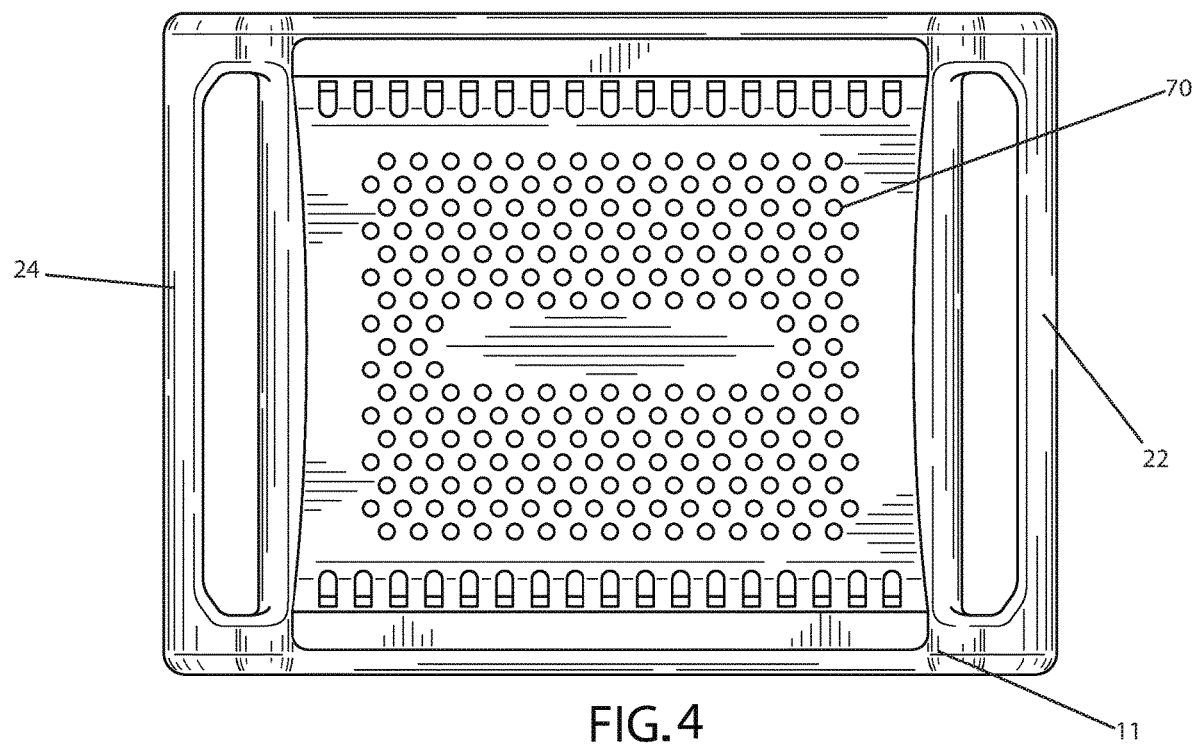
FIG. 4 is a front view of the device.

FIG. 4 is a front view of the chiller device which shows handles 22 and 24 as well as a front grill 70. The front grill 70 can be extended out in front of the body of the device leaving a space or a gap between the grill and the body 11.

Figure 5:
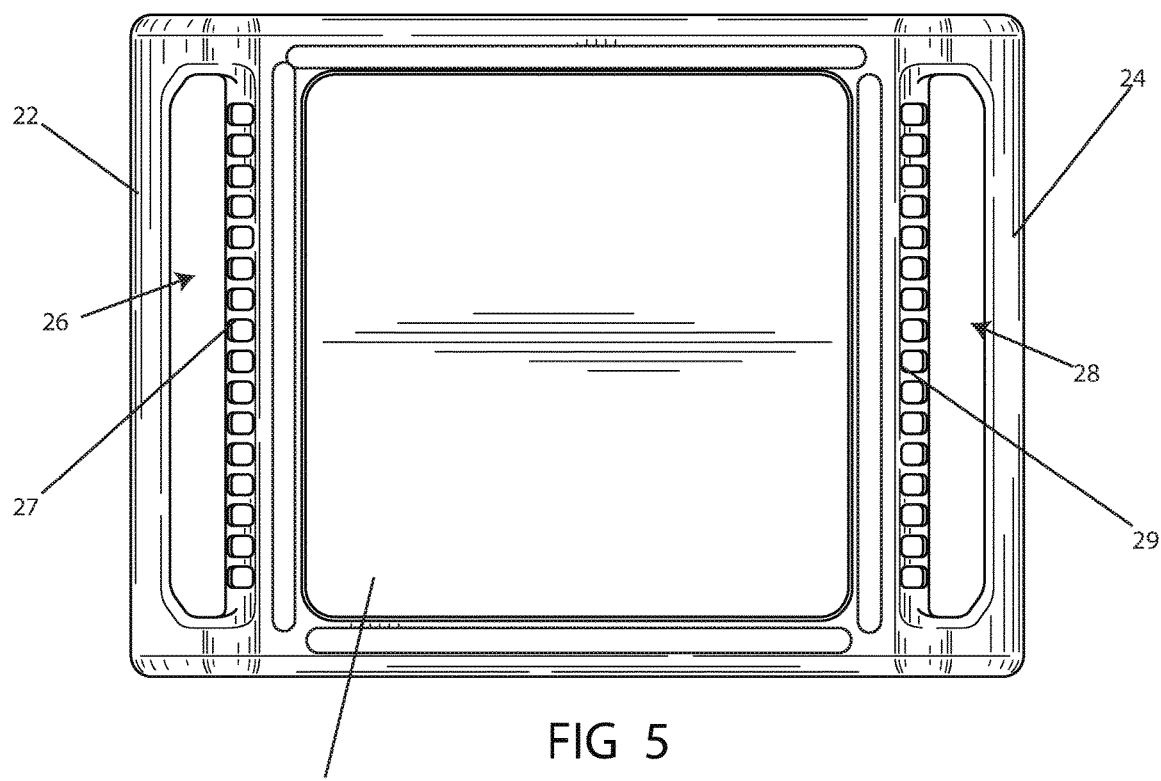
FIG. 5 is a back view of the device.

FIG. 5 is a view of the chiller side of the device with chiller plate 30 being shown. This view shows vents 27 and 29 as well as gaps 26 and 28 between respective handles 22 and 24. The chiller plate can be made from any suitable material such as a metal such as copper, aluminum, or any other type of suitable material.

Figure 6:
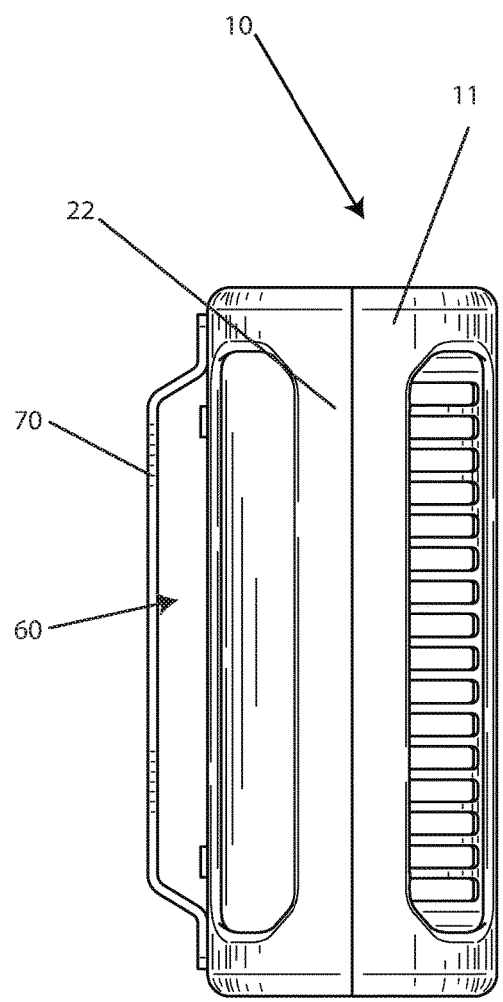
FIG. 6 is a right-side view of the device.
Figure 7:
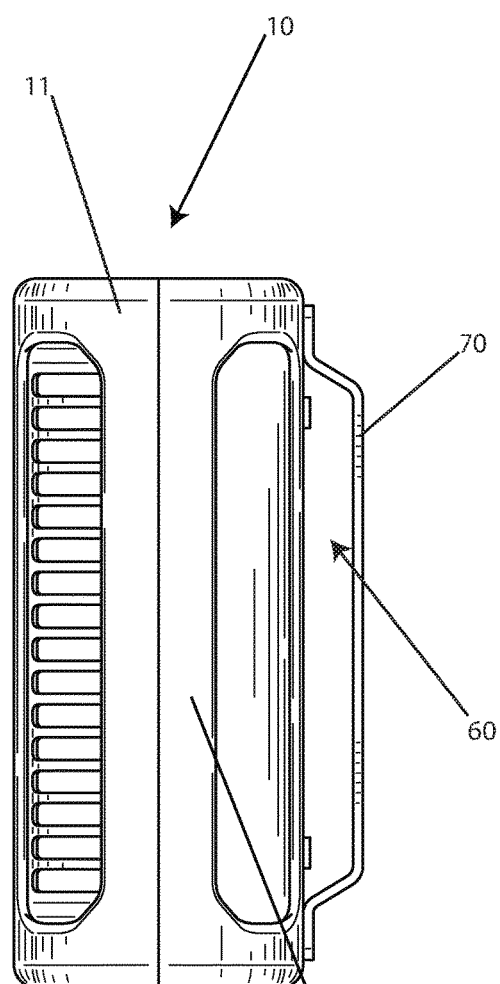
FIG. 7 is a left-side view of the device.

FIG. 6 is a right side view of the device 10 showing handle 22 and grill or vents 70. In addition, there is shown a gap 60 between grill 70 and body 11. FIG. 7 shows a left side view as well which shows handle 24 instead of handle 22 as well as grill 70 body 11, gap 60.

Figure 8:
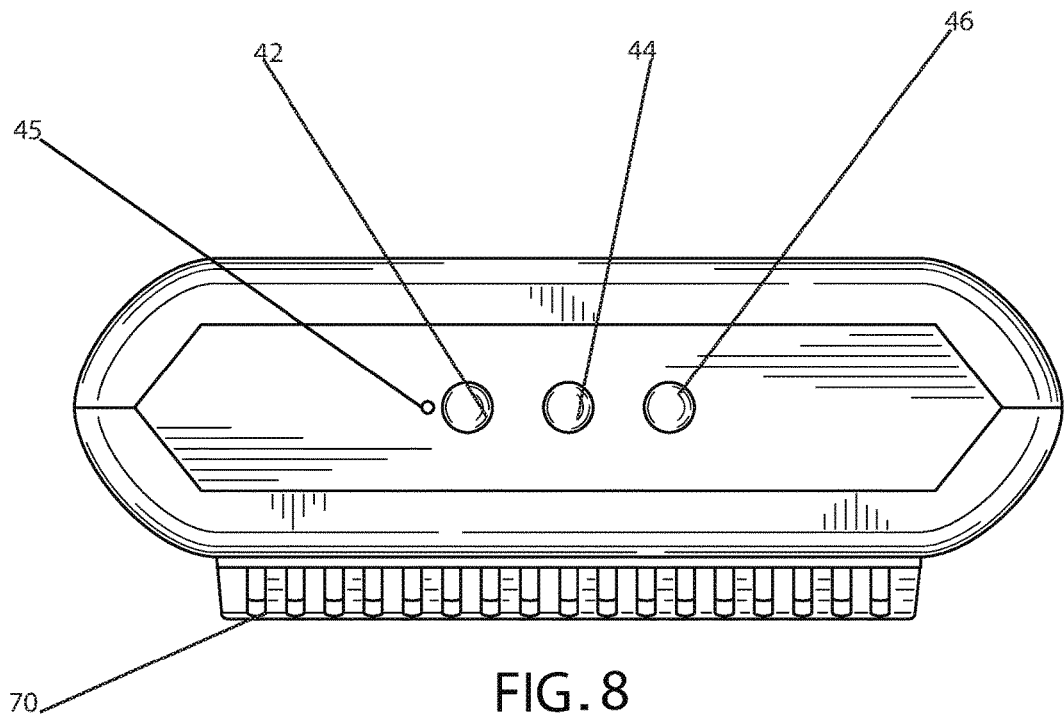
FIG. 8 is a top view of the device.
Figure 9:
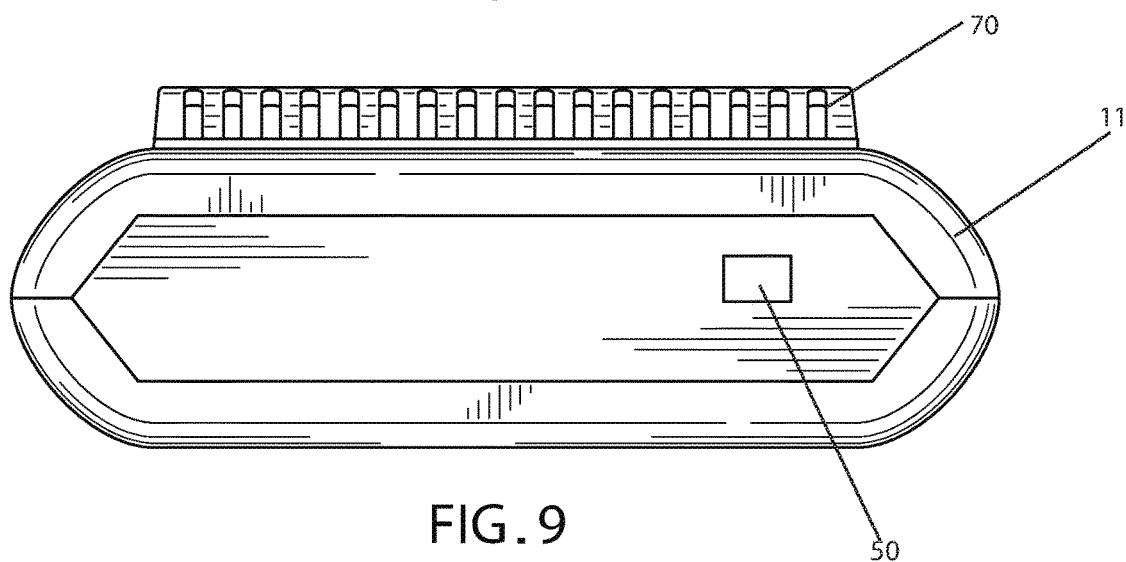
FIG. 9 is a bottom view of the device.

FIG. 8 is a top view of the device 10 including body 11, grill 70, an on/off switch or button 42, and up switch or button 44, and a down switch or button 46. The on/off button is in communication with light 45, wherein this light is used to indicate whether 1 the device is on or off. FIG. 9 is a bottom view which shows a power port 50 which allows the device to be connected to a power supply so that the device can be charged/recharged.

Figure 10:
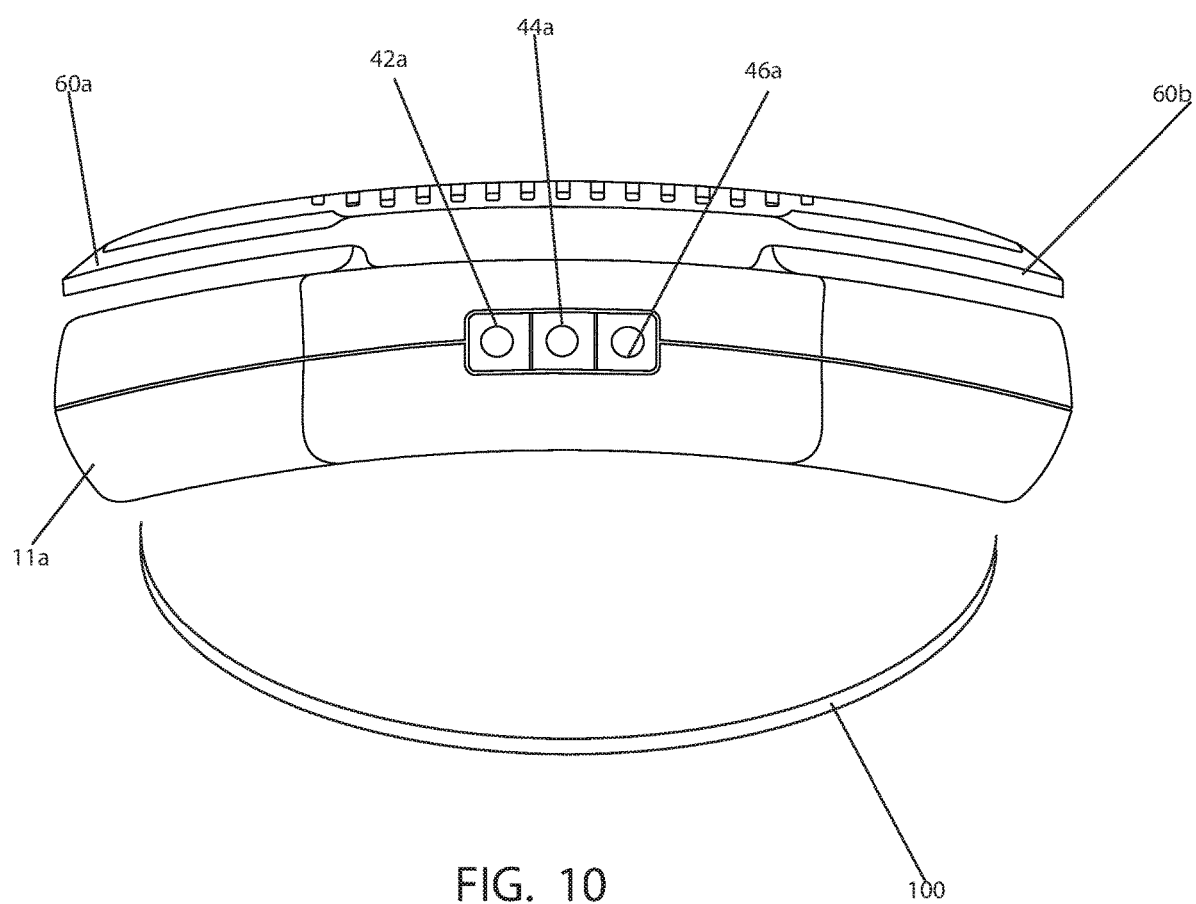
FIG. 10 is a top view of another embodiment of the device.

FIG. 10 is a top view of another embodiment, 10a, which shows another body design of a housing 11a, as well as a grill having wings 60a and 60b that are spaced apart from the body or housing 11a. There is an on/off button 42a, an up button 44a, and a down button 46a as well. There is also a strap 100 which can be coupled to the device, wherein this strap can be coupled around the handles (not shown but similar to handles 22 and 24 in FIG. 1).

Figure 11:
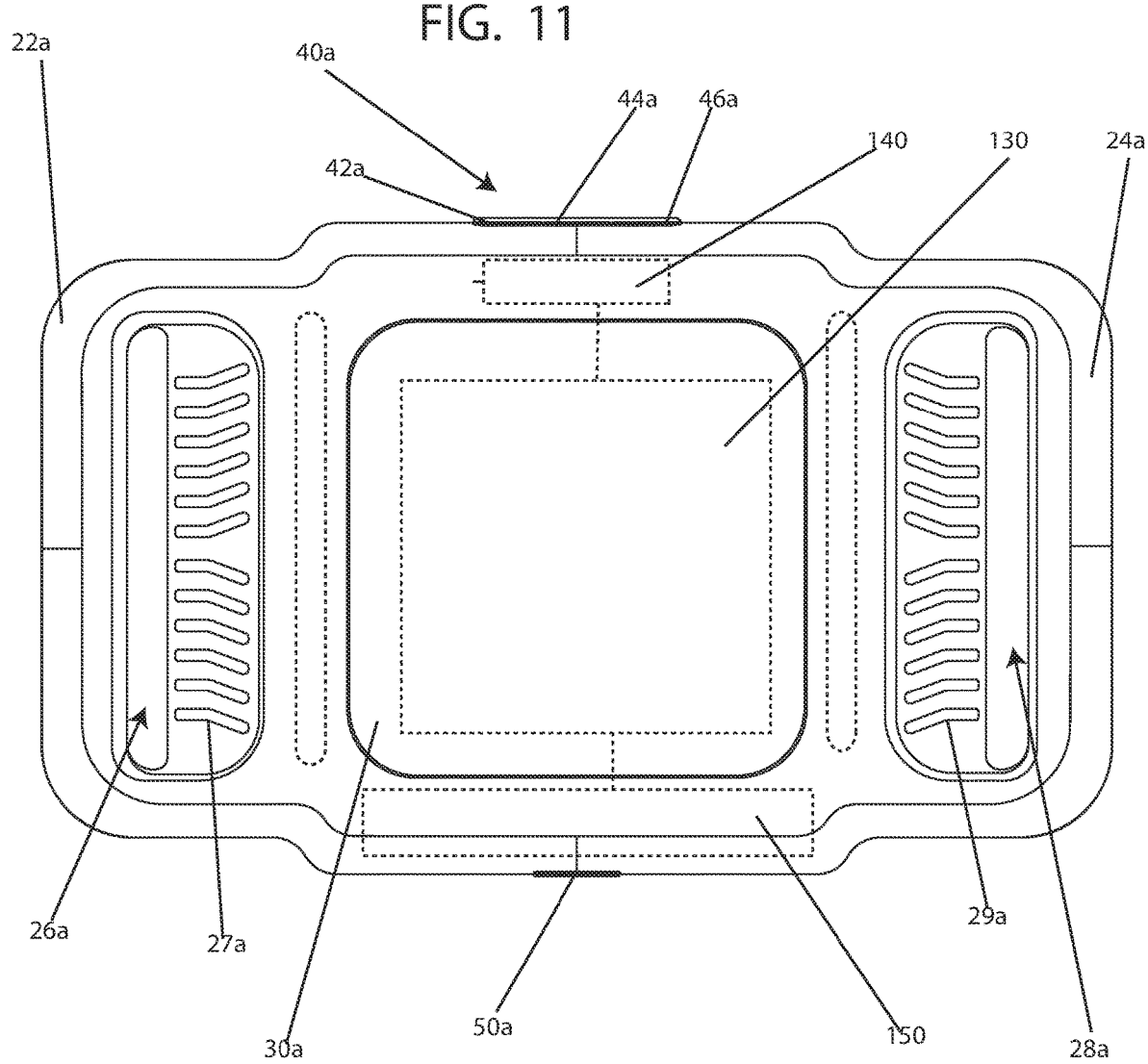
FIG. 11 is a back view of the device with the components in dash-dotted lines.

FIG. 11 is a front view of the device which shows some of the inner electronic components. For example, there is shown chiller 130 which is positioned adjacent to cold plate 30a. Cold plate 30a is configured to be placed on a person's body such as on their stomach or thigh area to essentially chill away the fat on a person's body. A controller 140 is positioned adjacent to controller/buttons 40a such that when the controller/buttons 40a are pressed, it either activates chiller 130 or cools chiller to a lower temperature or warms chiller 130 up to a higher temperature depending on which button is pressed. In addition, disposed inside this housing 11a is a battery 150 which is configured to store energy from the battery plug connection 50a. These internal components such as chiller 130, controller 140 and battery 150 are present in both the embodiment 10a as well as in the embodiment 10. Vents 27a and 29a are shown as curved vents which are angled instead of straight.

As shown in FIG. 12A, the device can also have a fan 149 disposed behind the chiller 130. Chiller 130 can be in the form of an aluminum or other type of conductive metal which is formed as a ribbed surface shown in FIG. 12B. Each of the ribs 131 of chiller is offset by an empty channel inside. Both the chiller and the fan can be powered by either a battery 150 or a transformer 151 (See FIG. 12B) coupled to an AC power source for direct electrical power.

This device can be constructed so as to be easy to use, portable and adaptable so as to accommodate straps and other devices as well.

FIG. 13 is a view of another embodiment 200. In this view there is a chiller or heat conductive plate 235 which is chilled by a chilling block (not shown) inside of a housing 201. Housing 201 is an outer housing that is similar to housing 11 shown in FIG. 1.

With this design, there are a plurality of lights or light emitters in array strips positioned around a chilling plate 235. These strips include a first strip 210, a second strip 220, a third strip 230, and a fourth strip 240. Each of these strips contains a series of lights such as LED's or other types of emitters which in a first embodiment emit infrared light which is configured to heat the pores of the skin around the chilling plate. The heating of the pores and the skin surface around the chilling plate allows for better contact and contraction of the skin under the chilling plate when the device is applied. Infrared light when emitted through and below the skin can also be used as a fat reducer. Alternatively, in another embodiment, the light strips could be ultraviolet light emitting strips, wherein these ultraviolet light emitting strips are configured to emit ultraviolet light which is configured to reduce fat cells in the body. Alternatively, the light strips such as strips 210, 220, 230 and/or 240 can be configured to emit a blue light that is not yet ultraviolet light for use in fat loss as well. Alternatively, in another embodiment the light strips can be alternating light strips of any one of infrared light, ultraviolet light or blue enriched light.

In addition, in the subsequent embodiments, each of the light strips are configured to be any one of ultraviolet light emitting strips, infrared light emitting strips or blue light emitting strips. In addition, disposed in or coupled to housing 201 is an interface 350, as well as a power input 341. Interface 350 is configured to allow the user to turn on the chiller, select the temperature of the chiller and/or turn on the light strips 210, 220, 230, and 240.

Figure 14:
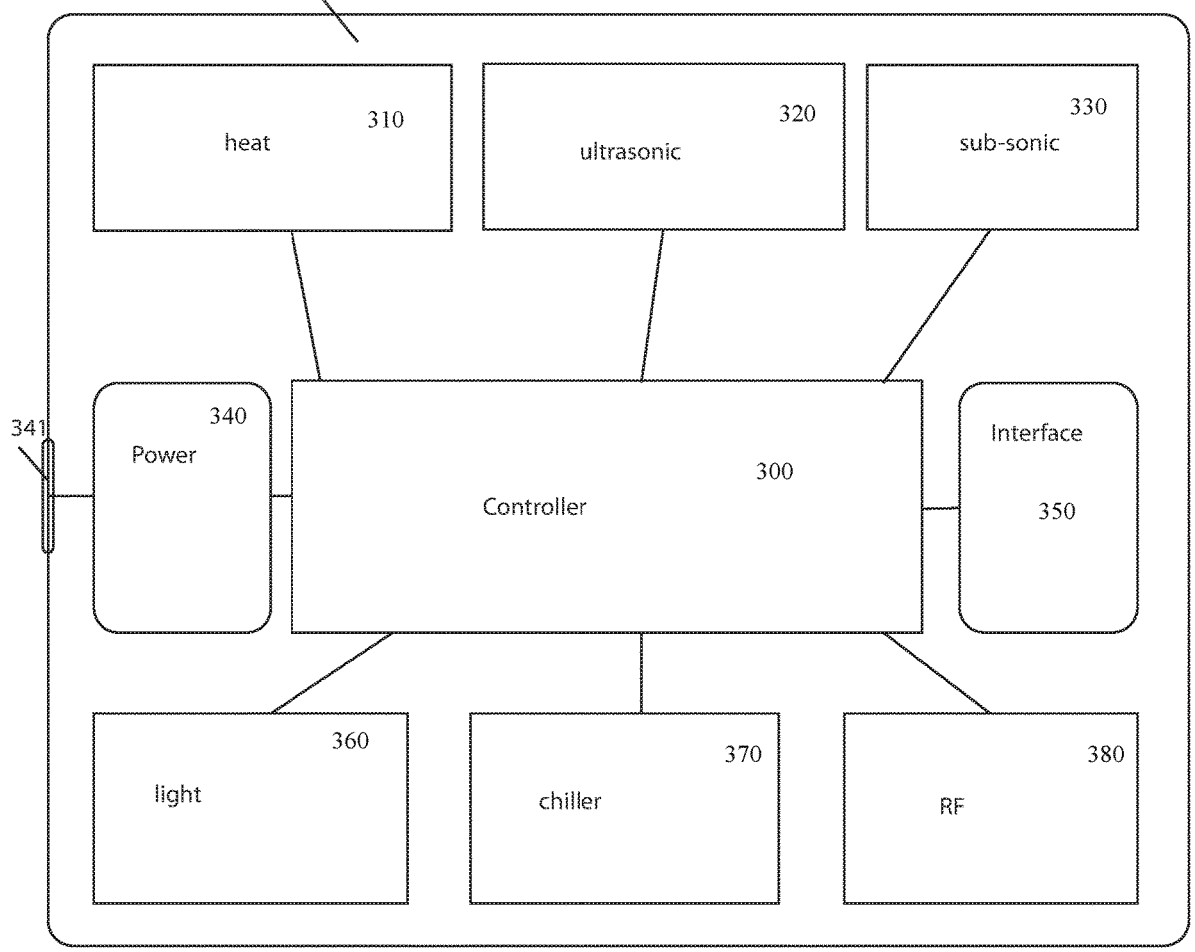
FIG. 14 is a schematic block diagram of another embodiment.

FIG. 14 is a view of the components which are configured to be selectively housed within housing 201. For example, in any one of the following embodiments there are any one of a heat emitter 310, an ultrasonic transducer 320 configured to emit ultrasonic vibrations, a sub sonic transducer 320 configured to emit sub sonic vibrations, a controller 300, a power input 341 coupled to a power supply 340, an interface 350 configured to allow a user to send instructions to controller 300, a RF (radio frequency) emitter 380, a chiller emitter 370, and a light emitter 360 which is configured to control light arrays or strips 210, 220, 230, and 240. The term sub sonic is a rate of vibration that is at any rate lower in frequency than at an ultrasonic frequency.

Figure 15:
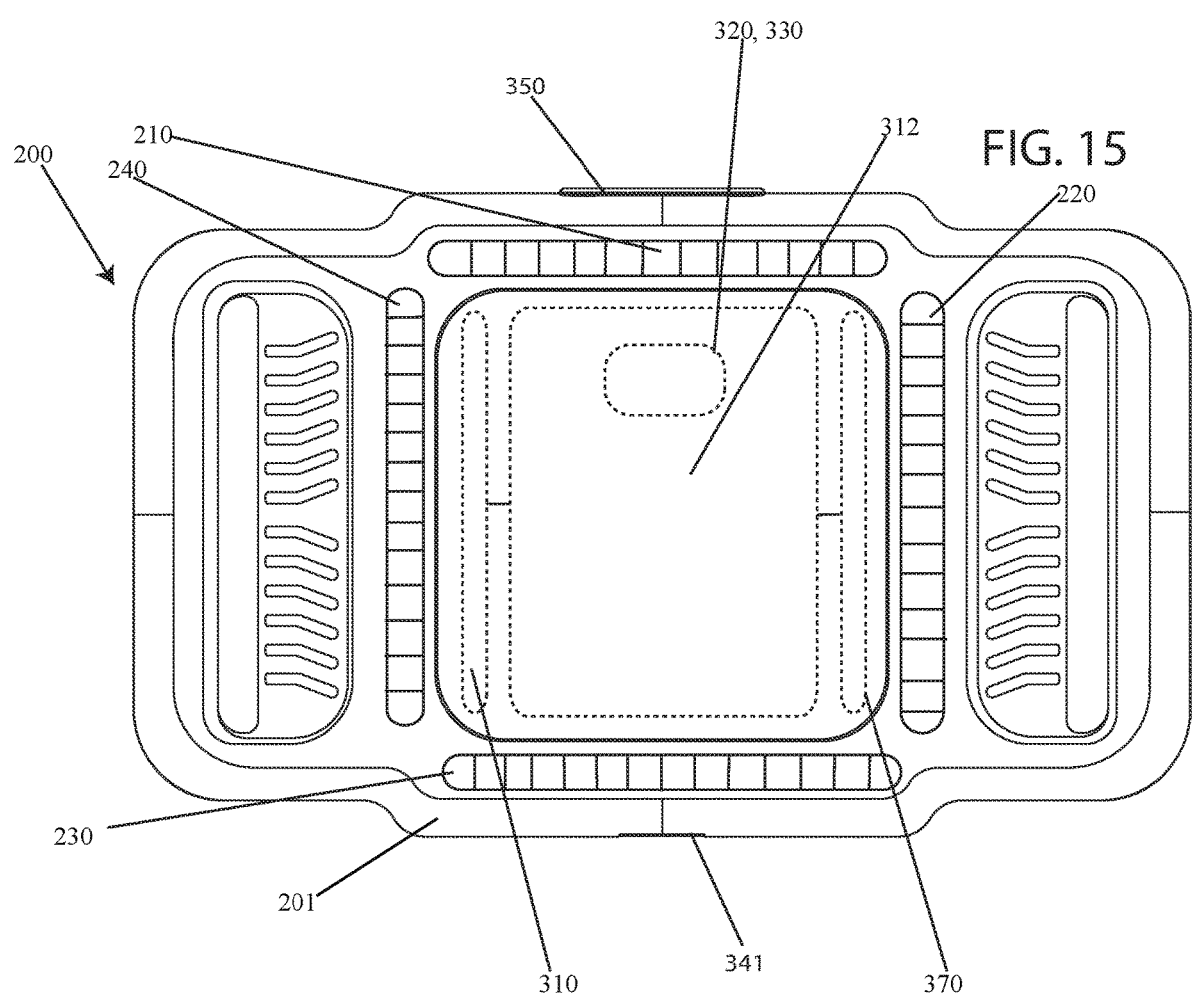
FIG. 15 is another view of another embodiment.

Any one of these components can be housed in housing 201 in any suitable combination. For example, disposed inside of housing can be both a heat emitter 310 as well as a chiller 370. Alternatively disposed inside of housing 201 can be a chiller 370 and an ultrasonic transducer 320. In another embodiment could be a chiller 370, an ultrasonic transducer 320, and a light emitter 360. In another embodiment could be a chiller 370, a ultrasonic transducer 320a light emitter and a radio frequency (RF) emitter 380 all configured to simultaneously emit different temperatures and/or signals configured to remove fat. FIGS. 15-19 show different examples of the different embodiments formed from these combinations. For example, FIG. 15 shows one embodiment which shows embodiment 200 having housing 201 wherein coupled to the housing 201 are a plurality of light arrays or strips 210, 220, 230, and 240. As indicated above these light strips or arrays in a variety of different embodiments are configured to emit any one of ultraviolet light, blue light, and/or infrared light. In addition, there is disposed below a temperature conducting plate such as plate 235 is a heat conductive block 312. Heat conductive block can be configured to be made as a chilling block or as a heating block depending on the driving mechanism. For example, coupled to heat conductive block 312 is any one of a heat emitter 310 or a chiller emitter 370. An interface 350 is shown which is configured to send signals to a controller such as controller 300 (not shown but present, see FIG. 14). There is also a power input 341, as well as a transducer which can be any one of an ultrasonic transducer/emitter 320 and/or a subsonic transducer/emitter 330. The ultrasonic transducer 320 is configured to emit vibrations or waves in the ultrasonic range while the subsonic transducer or emitter 330 is configured to emit vibrations or waves in a subsonic range.

Figure 16:
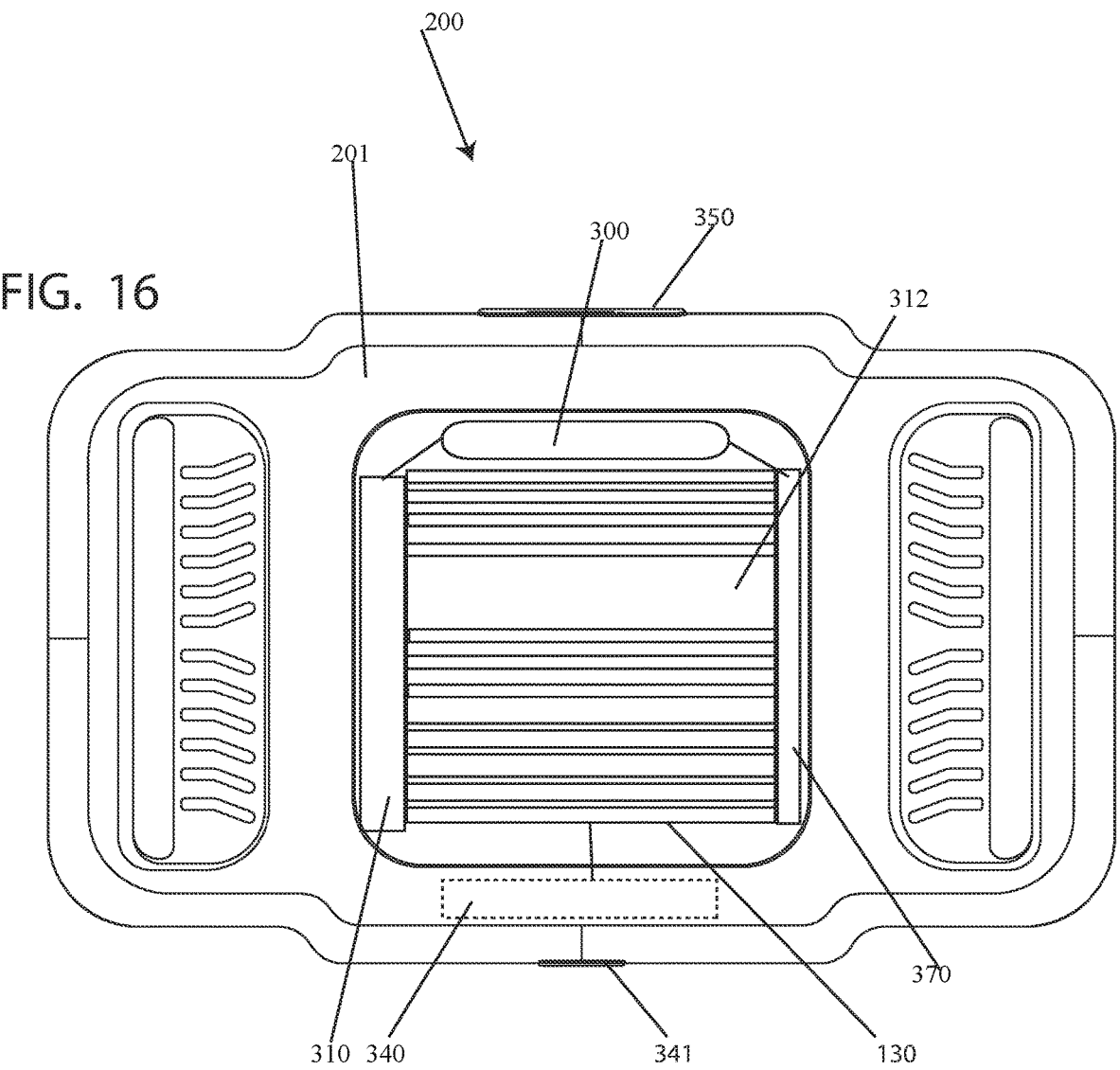
FIG. 16 is another view of another embodiment.

FIG. 16 is a view of another embodiment which includes conductive plate 235 removed for further viewing. In this view there is shown heat conductive block 312. Heat conductive block 312 and heat conductive plate can be made of any suitable heat conductive material such as copper, aluminum, or any other suitable metal, material or alloy configured to conduct heat to create either a chilled or a heated surface. Coupled to heat conductive block 312 is either a heat emitter 310 or a chiller emitter 370. Heat emitter can be any form of suitable heat emitter such as a coil or resistor which when powered heats up to conduct heat into heat conductive block. Alternatively, chiller emitter can be any type of suitable chilling device such as a compressor or other suitable chilling solution which conducts a chilled temperature (draws heat away from) heat conductive block 312 to drop the temperature of plate 235 to a temperature such as below −2 degrees C. or alternatively −4 degrees C., alternatively −6 degrees C. any temperature range between −2 degrees C. and −6 degrees C. or any other suitable chilling temperature. In addition, while a controller such as controller 300 and power supply such as power supply 340 are present in each of the embodiments shown in FIGS. 13-19 they are also shown here as well. For example, power supply 340 is shown electrically coupled to power input 341. Thus, power is received into the housing through power input 341, into power supply 340 and is configured to power all of the components including but not limited to controller 300.

Controller 300 can be any suitable form of controller and/or processor which may have suitable memory such as RAM/and/or ROM configured to hold programs or sets of instructions, as well as suitable processing to process the instructions received from input or interface 350.

Figure 17:
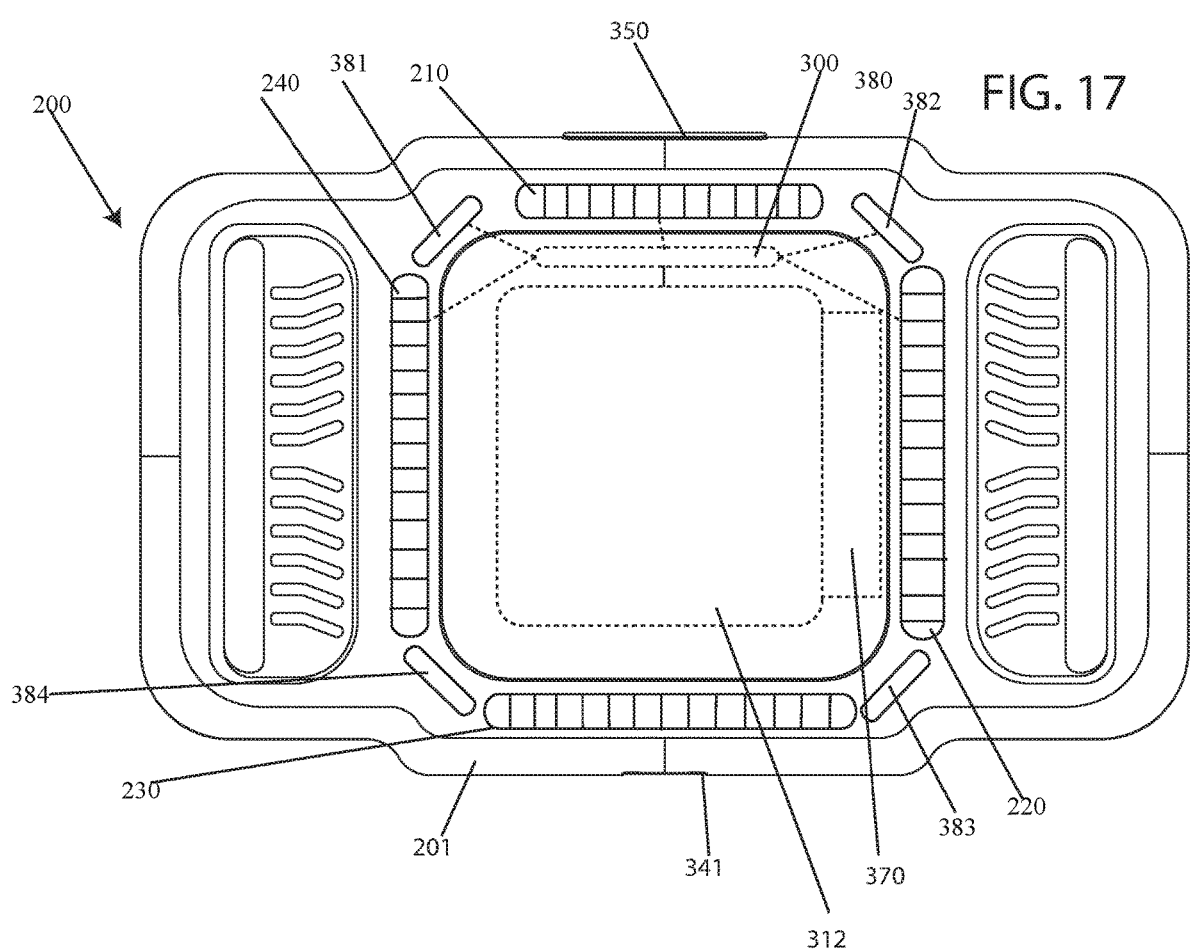
FIG. 17 is another view of another embodiment.

FIG. 17 shows another embodiment 200 which shows a heat conductive block 312 disposed inside of a housing 201. Disposed inside of this housing are different RF frequency emitters 380 comprising emitters 381, 382, 383, and 384 disposed between light strips and/or arrays 210, 220, 230 and 240. The light strips 210, 220, 230 and 240 along with the emitters 380 are controlled by controller 300. Furthermore, in this embodiment conductive block 312 is in communication with a chiller 370 (not shown). In this embodiment, the device is configured to emit any one of ultraviolet light, blue light and/or infrared light as well as providing RF transmission and/or cooling contact to a person's body to provide therapy treatment to reduce the subcutaneous fat when the housing 201 is placed on a user's body such that when a conductive plate 235 is placed on a user's stomach.

Figure 18:
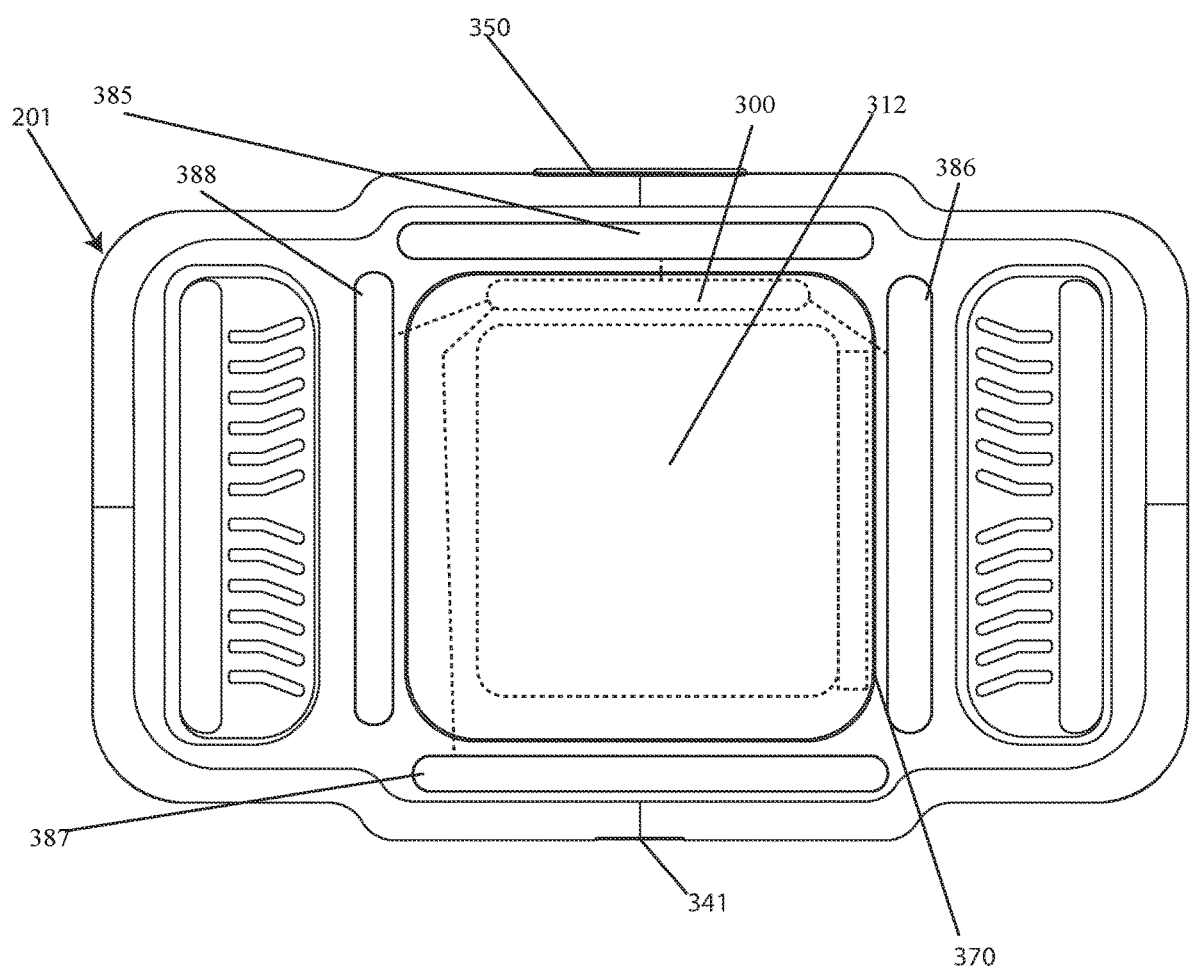
FIG. 18 is another view of another embodiment.

FIG. 18 is another embodiment which shows a heat conductive block 312 coupled to a chiller (not shown). Wherein a conductive plate 235 is also removed. A plurality of larger RF emitters 385, 386, 387, and 388 are disposed in housing 201 and configured to emit a radio frequency signal which when transmitted into a user's body results in therapeutic reaction to the users fat cells. In addition, with the presence of a conductive block being chilled by a chiller such as chiller 370 see FIG. 14, the combined therapeutic sensation of RF and chilling can result in therapeutic reaction of reducing or destroying fat cells in a user's body.

Figure 19:
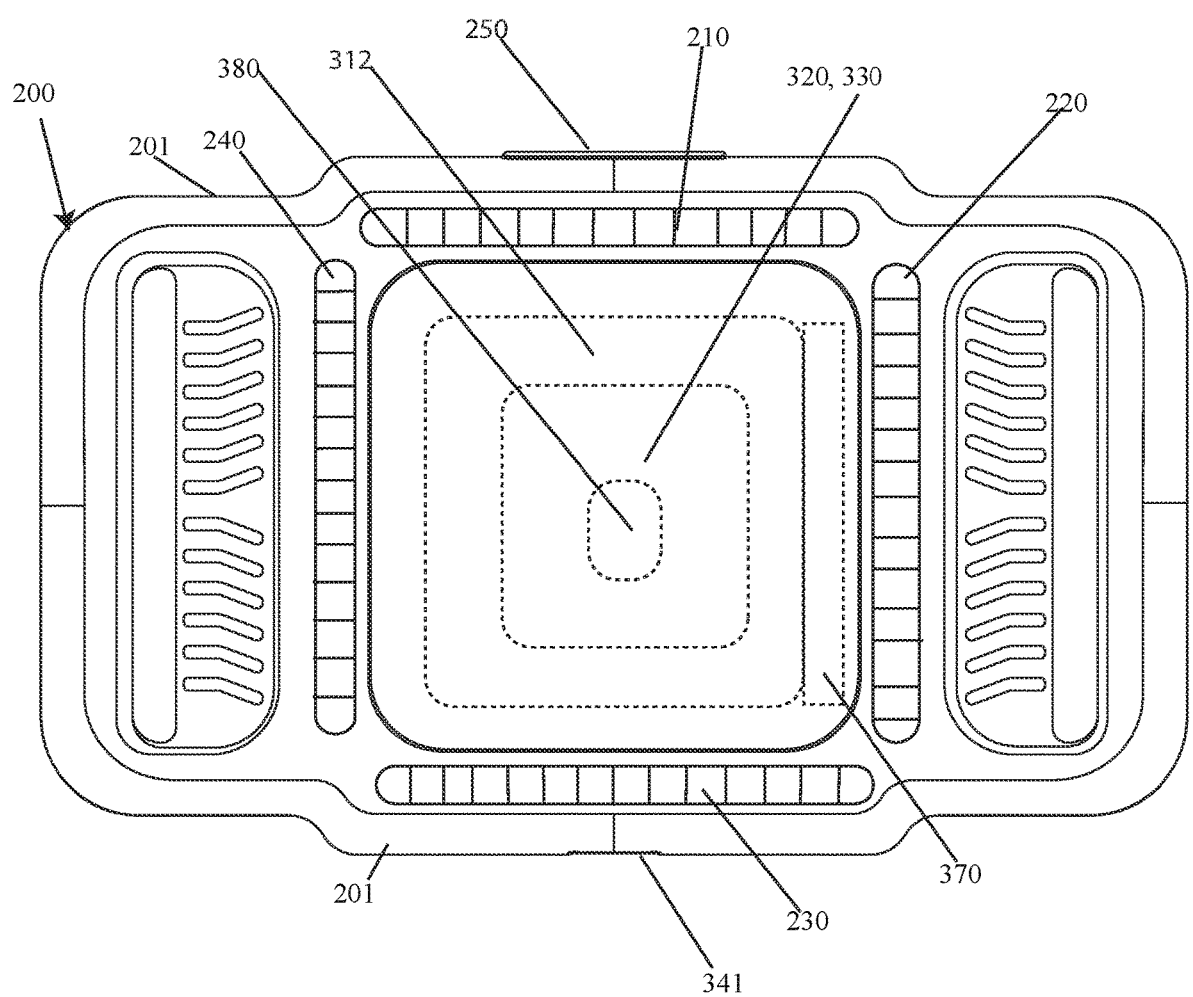
FIG. 19 is another view of another embodiment.

FIG. 19 shows another embodiment which shows housing 201 having a RF emitter 380 disposed inside of the housing, along with a chiller which is coupled to a heat conductive block 312 (not shown). In addition, there is also an ultrasonic transducer 320 disposed inside of housing 201 as well. Furthermore, there is an array of lights 210, 220, 230 and 240 which can be any one of infrared lights, ultraviolet lights and/or blue lights configured to provide therapeutic benefit of reducing fat on a user. There is also shown a power input 341 as well as an interface 350 for providing instructions to a controller 300.

Figure 20:
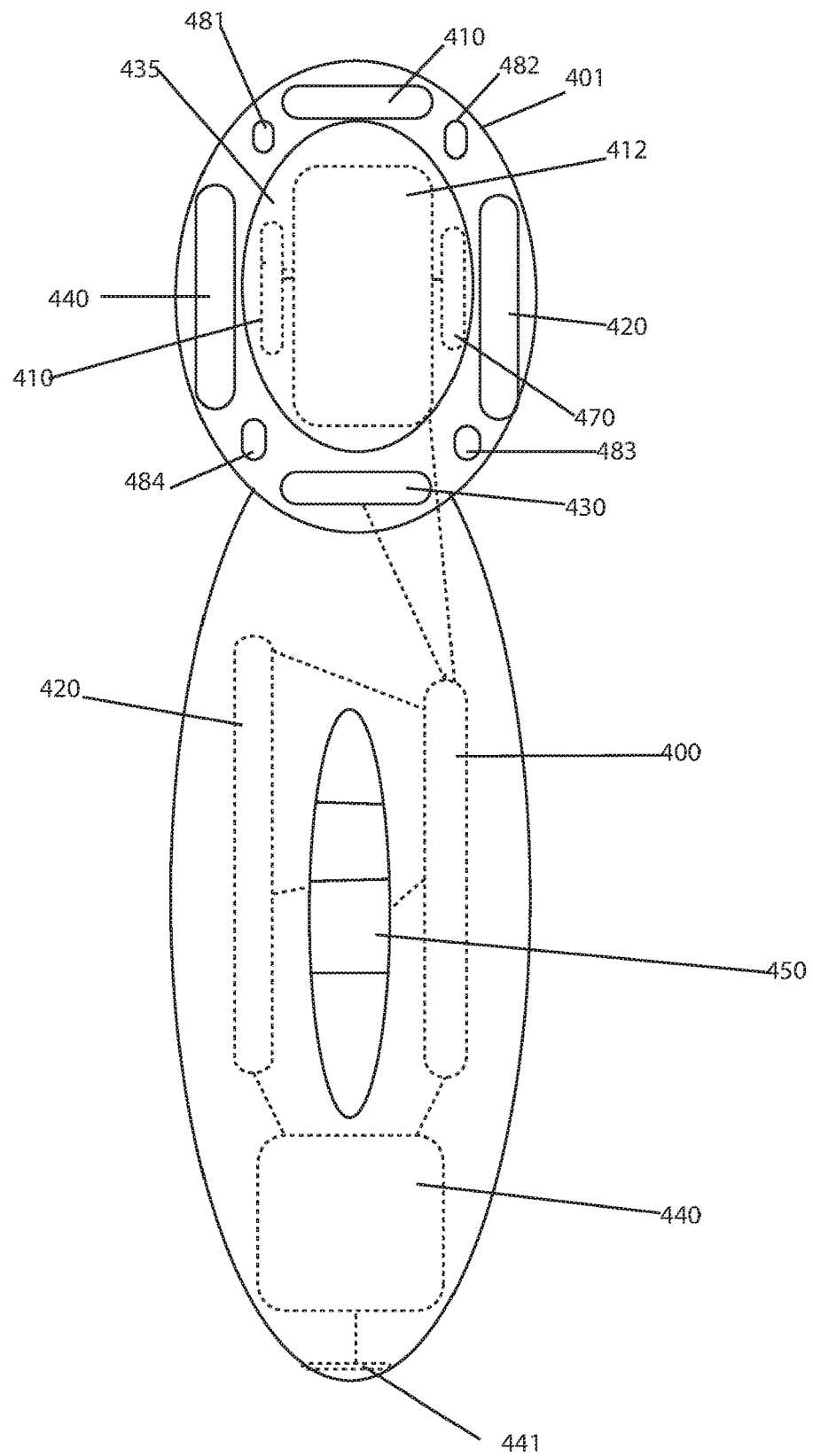
FIG. 20 is another view of another embodiment.

FIG. 20 is another view of another embodiment. For example, there is a housing 401 which is configured in a more oval shape that is more compact. With this design, it is configured for therapeutic action for fat loss around the chin and face of a user or targeted areas of a user. Disposed in or coupled to housing 401 are strips or arrays of lights 410, 420, 430 and 440. As with strips or arrays 210, 220, 230, and 240, these strips or arrays of lights are configured to emit any one of infrared light, ultraviolet light and or blue light. For example, in one embodiment the strips emit ultraviolet light. In another embodiment the strips emit infrared light, in another embodiment the strips emit blue light. An addition, coupled to and/or disposed in housing 401 are RF emitters 481, 481, 483, and 484. These RF emitters are configured to emit radio frequency waves from the housing. In addition, there is a heat emitter 411 and a chiller or cold emitter 470 coupled to heat conducting block 412. Heat conducting block 412 is coupled to heat conducting plate 435. Heat conducting plate is configured to contact a user's skin to either draw heat away from the user's skin or apply heat to the user's skin. All of these components are in communication with a controller 400. Controller 400 is disposed in housing 401 and is in communication with interface 450. Controller 400 is similar to controller 300 as indicated above. In particular the communication and connection between the components in this embodiment is similar to the block diagram shown in FIG. 14. In addition, disposed inside of housing 401 is an ultrasonic transducer configured to provide ultrasonic vibrations as well. Interface 450 is configured to send signals to controller 400 to selectively activate any one of the above identified components. There is also a power supply 440 and a power input 441.

Figure 21:
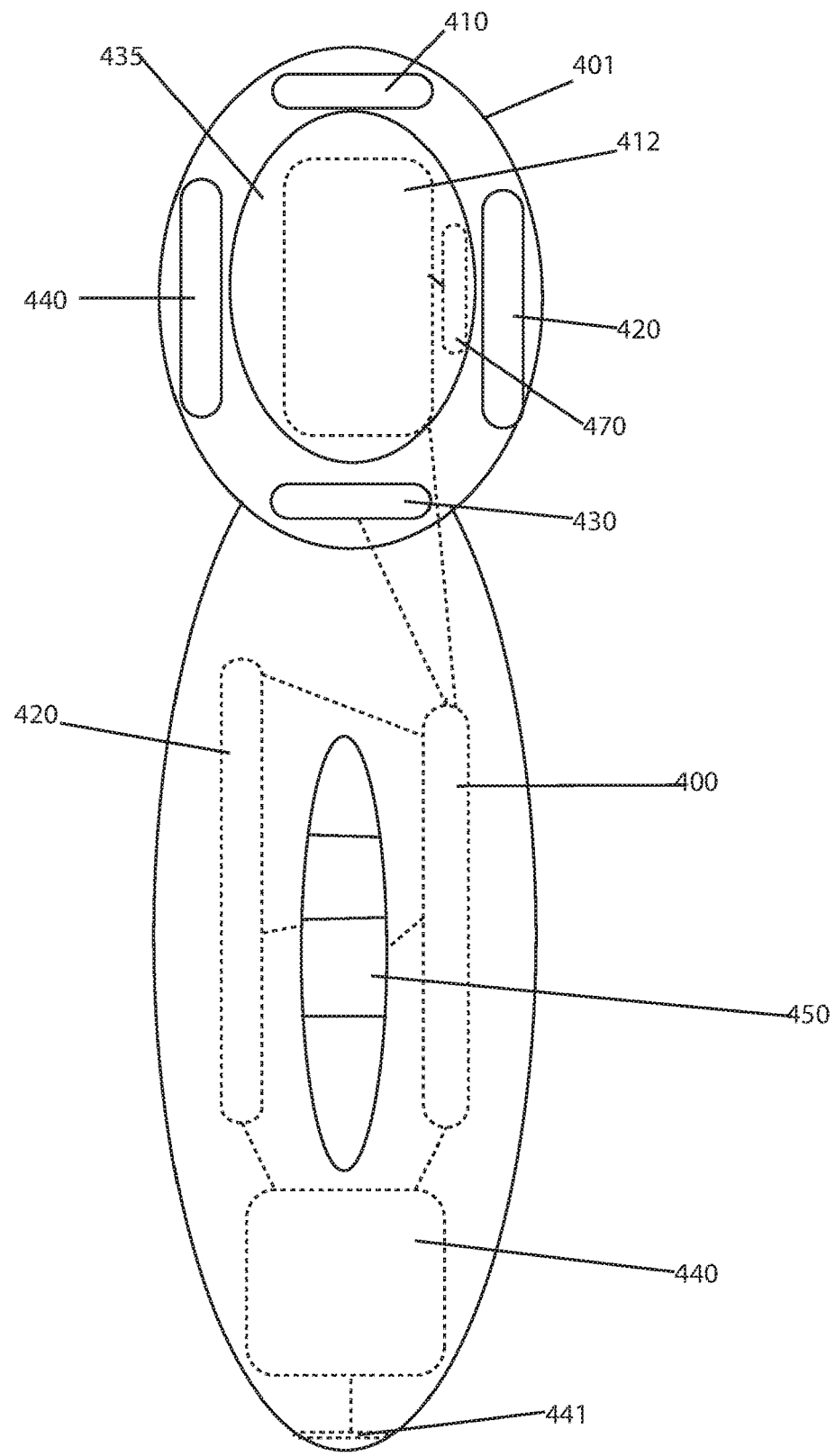
FIG. 21 is another view of another embodiment.

FIG. 21 shows another embodiment which is similar to the embodiment shown in FIG. 20 however this embodiment does not include a heat emitter 411, RF emitters 481, 482, 483, and 484. However, the other components listed above in FIG. 20 are still present.

Thus, there can be different types of treatment apparatus which are configured to treat a user for treatment of fat loss, particularly subcutaneous fat loss. The different treatment elements which are configured to emit light, cold, heat, radio frequency, ultrasonic or sonic vibrations can be combined in any array of arrangements inside of a housing to provide a therapeutic stimulation to a person's body.

Accordingly, while at least one embodiment of the present invention have been shown and described, it is to be understood that many changes and modifications may be made thereunto without departing from the spirit and scope of the invention as defined in the appended claims.

What is claimed is:
1. A cold treatment apparatus configured to cool an object comprising:
 a) at least one housing;
 b) at least one chiller disposed in said at least one housing;
 c) at least one heat conductive plate coupled to said at least one chiller and to said at least one housing and disposed in a center region of said at least one housing;
 d) at least one controller coupled to said at least one housing, said at least one controller configured to control a temperature of said at least one chiller;
 e) at least one light emitter coupled to the at least one housing;
 f) at least one handle coupled to said at least one housing; and
 g) a plurality of RF emitters;

wherein said at least one light emitter comprises a plurality of light emitters, wherein said plurality of RF emitters and said plurality of light emitters are spaced around said at least one housing peripherally surrounding an outer perimeter of said at least one heat conductive plate in an alternating manner.

2. The cold treatment apparatus as in claim 1, wherein said at least one light emitter is configured to emit infrared light.

3. The cold treatment apparatus as in claim 1, wherein said at least one light emitter is configured to emit ultraviolet light.

4. The cold treatment apparatus as in claim 3, further comprising at least one radio frequency (RF) emitter of said plurality of RF emitters coupled to the at least one housing.

5. The cold treatment apparatus as in claim 4, further comprising at least one subsonic transducer configured to vibrate at least a portion of said at least one housing at a subsonic frequency.

6. The cold treatment apparatus as in claim 1, wherein said at least one controller is for controlling the temperature of said at least one chiller and for controlling whether said at least one light emitter emits a light.

7. The cold treatment apparatus as in claim 1 further comprising at least one ultrasonic transducer configured to vibrate at least a portion of said at least one housing at an ultrasonic frequency.

8. The cold treatment apparatus as in claim 1, further comprising at least one heat emitter and at least one heat conductive block both coupled to said at least one housing, wherein said at least one heat emitter is configured to conduct heat to said at least one heat conductive block to heat said at least one heat conductive plate.

9. The cold treatment apparatus as in claim 1, wherein the at least one housing is a hand-held housing.

10. The cold treatment apparatus as in claim 9, wherein said at least one heat conductive plate is rounded.

11. The cold treatment apparatus as in claim 1 further comprising a power supply wherein said power supply comprises a transformer.

12. A therapeutic fat treatment apparatus configured to treat a patient comprising:
at least one housing;
at least one heat conductive plate coupled to the at least one housing,
at least one ultrasonic transducer configured to vibrate said at least one housing at an ultrasonic frequency;
at least one controller coupled to said at least one housing, said at least one controller being configured to control a vibration rate of said at least one ultrasonic transducer; and
at least one light emitter coupled to the at least one housing; and
a plurality of RF emitters;
wherein said at least one light emitter comprises a plurality of light emitters, wherein said plurality of RF emitters and said plurality of light emitters are spaced peripherally surrounding an outer perimeter of said at least one heat conductive plate in said at least one housing in an alternating manner.

13. The therapeutic fat treatment apparatus as in claim 12, wherein said at least one light emitter is in communication with said at least one controller wherein said at least one controller is configured to selectively turn on said at least one light emitter.

14. The therapeutic fat treatment apparatus as in claim 12, further comprising at least one heat conductive block coupled to the at least one housing and at least one cold emitter configured to draw heat from the at least one heat conductive plate and said at least one heat conductive block to provide a chilled interface which is configured to have a temperature below -2 degrees Celsius.

* * * * *